(12) United States Patent
Vikholm et al.

(10) Patent No.: US 7,510,882 B2
(45) Date of Patent: *Mar. 31, 2009

(54) METHOD AND BIOSENSOR FOR ANALYSIS

(75) Inventors: Inger Vikholm, Tampere (FI); Janusz Sadowski, Tampere (FI)

(73) Assignee: Bionavis Ltd., Helsinki (FI)

( * ) Notice: Subject to any disclaimer, the term of this patent is extended or adjusted under 35 U.S.C. 154(b) by 10 days.

This patent is subject to a terminal disclaimer.

(21) Appl. No.: 11/785,238

(22) Filed: Apr. 16, 2007

(65) Prior Publication Data

US 2007/0254382 A1 Nov. 1, 2007

Related U.S. Application Data

(62) Division of application No. 10/164,652, filed on Jun. 10, 2002, now Pat. No. 7,332,327.

(30) Foreign Application Priority Data

Sep. 24, 2001 (FI) ................................. 20011877

(51) Int. Cl.
*G01N 33/543* (2006.01)
*G01N 33/551* (2006.01)
*G01N 33/552* (2006.01)
*G01N 33/553* (2006.01)

(52) U.S. Cl. .................. 436/518; 310/313 R; 310/340; 385/12; 385/129; 385/130; 422/57; 422/82.11; 435/287.2; 435/287.9; 435/288.7; 435/808; 435/962; 436/512; 436/164; 436/524; 436/525; 436/527; 436/810

(58) Field of Classification Search ........................ None
See application file for complete search history.

(56) References Cited

U.S. PATENT DOCUMENTS

| 4,775,637 A | 10/1988 | Sutherland et al. |
| 5,135,876 A | 8/1992 | Andrade et al. |
| 5,242,828 A | 9/1993 | Johnsson et al. |
| 5,322,798 A | 6/1994 | Sadowski |
| 5,492,840 A | 2/1996 | Malmqvist et al. |
| 5,677,196 A | 10/1997 | Herron et al. |

(Continued)

FOREIGN PATENT DOCUMENTS

DE 10002895 7/2001

(Continued)

*Primary Examiner*—Christopher L Chin
(74) *Attorney, Agent, or Firm*—Buchanan Ingersoll & Rooney PC (57) ABSTRACT

In a method for analysis biomolecules (3) attached to a solid surface of a substrate (1) are used for detecting the presence of analytes (4) in a sample by binding of the analytes to the biomolecules. The biomolecules (3) are attached directly to the surface of the substrate together with biomolecule-repellent molecules (5), which cover the surface between the biomolecules (3) to prevent nonspecific binding of analytes (4) and other biomolecules. The invention relates also to a biosensor where biomolecules (3) are attached directly to the substrate (1) together with biomolecule-repellent molecules (5), which cover the surface between the biomolecules (3) to prevent non-specific binding of analytes (4) and other biomolecules. The biomolecules (5) can be self-assembled hydrophilic polymers. One example of using the invention is immunological analysis using surface plasmon resonance (SPR).

18 Claims, 5 Drawing Sheets

U.S. PATENT DOCUMENTS 6,844,028 B2    1/2005   Mao et al.
7,332,327 B2 *  2/2008   Vikholm et al. .......... 435/287.2
2002/0102405 A1 8/2002   Chapman et al.

FOREIGN PATENT DOCUMENTS

EP    0485874    5/1992
WO    0065352    11/2000

* cited by examiner

METHOD AND BIOSENSOR FOR ANALYSIS

CROSS-REFERENCE TO RELATED APPLICATION

This application is a divisional of application Ser. No. 10/164,652, filed Jun. 10, 2002, now U.S. Pat. No. 7,332,327, which claims priority to FI 20011877, filed Sep. 24, 2001, both of which are incorporated herein by reference.

FIELD OF THE INVENTION

The present invention relates to a method for analysis. The invention also relates to a biosensor for carrying out the method.

BACKGROUND OF THE INVENTION

There is an increasing need for simple, rapid and easy-to-use sensors to aid clinical diagnosis and for environmental analysis.

The very specific and tight binding between antibodies and antigens has traditionally been measured in clinical laboratories by radioimmunoassay, solid phase enzymeimmunoassay and fluoroimmunoassay. Quantification of the antibody-antigen complex relies on a marker molecule, such as a radioisotope, an enzyme or a fluorescent probe. In most cases, the result is not obtained until several incubations, washing and separation steps have been performed.

Presently, immunosensors that can monitor antigen concentrations in real-time with the aid of an immobilized antibody and that do not require the use of labeled species are being developed. The lack of control over the orientation of the antibodies, however, limits the proportion of available binding sites when using conventional immobilization methods [Attili, B.; Suleiman, A.; *Microchemical Journal* 54 (1996) 174]. Site-specific immobilization, on the other hand, leads to higher activity. Options for controlled immobilization of antibodies include specific binding of the Fc region of the antibody to a protein A or protein G, covalent attachment through the free sulfhydryl group on the anti-body Fab'-fragments onto supported layers and biotinylated antibodies coupled onto a surface by biotin/(strept)avidin chemistry [Morgan, H.; Taylor, D. M.; *Biosensors & Bioelectronics* 7 (1992) 405; Vikholm, I.; Albers, W. M.; *Langmuir* 14 (1998) 3865; Fischer, B.; Heyn, S. P.; Egger, M.; Gaub, H. E.; *Langmuir* (9) (1993) 136; Schönhoff, M.; Lösche, M.; Meyer, M.; Wilhelm, C.; *Progr. Colloid Polym. Sci.* (1992) 243; Krull, U. J.; Brown, R. S.; Vandenberg, E. T.; Heckl, W. M.; *J., Electr. Microscopy Technique* 18 (1991) 212; Heyn, S. P.; Egger, M.; Gaub, H. E.; *J. Phys. Chem.* 94 (1990) 5073].

It has, however, recently been shown that Fab'-fragments can be adsorbed directly onto gold with high epitope density [O'Brien, J.; Jones, V.; Porter, M.; *Anal. Chem.* 72 (2000) 703]. The high surface energy of metal surfaces normally leads to denaturation of biomolecules with a decrease in activity. The mechanism of adsorption has been studied extensively and involves hydrophobic interaction between the surface of the material and hydrophobic patches on the surface of the biomolecule. After the initial adsorption, the protein may denaturate and unfold to expose more hydrophobic groups and thus lose its activity [Andrade, J. D., Hlady, V., *Adv. Polym. Sci.* 79 (1986) 1-63].

Patent documents describing the use of various linker molecules which form a monolayer on a surface for attachment of biomolecules to make a bio-sensor where the detection can be performed by surface plasmon resonance, include U.S. Pat. No. 5,242,828 and European Patents nos. 442922 and 485874.

Receptor molecules, which could be attached onto the transducer interface in an oriented and reproducible manner with minimal unfolding, would enable optimal preservation of the activity and specificity and could be used in sensor applications requiring high sensitivity. A site-directed immobilization of the receptor molecules would ensure maximal binding efficiency.

Another problem that has to be overcome in biosensor applications is non-specific binding. Biorepellent surfaces have become a subject of great interest in fields such as biochemistry, biology, biotechnology, and health care, because of the need to control the interaction of biomolecules and cells with various surfaces. Protein-repellent surfaces are crucial to blood-contacting implant devices, membranes for separation processes, chromatographic supports, contact lenses, and blood and protein storage devices.

Biomolecule repellent surfaces can be prepared by immobilizing non-ionic, hydrophilic polymers, such as poly(acrylamide), poly(N,N-dimethyl-acrylamine), poly(vinylalcohol), ethylene-vinylalcohol copolymer, poly(hydroxy-ethyl methacrylate), poly(ethyleneoxide) and poly(ethyleneglycol) [Köberle, P.; Laschewsky, A.; van den Boogaard, D.; *Polymer* 33 (1992) 4029; Saito, N.; Sugawara, T.; Matsuda, T.; *Macromolecules* 29 (1996) 313]. The resistance to adsorption of proteins is based on the entropic and hydrodynamic repulsion of the flexible molecular chains of the biorepellent surface and the biomolecules of a solution being higher than the combined forces of attraction. Polymers have been adsorbed by physical coating, chemical coupling or graft copolymerisation.

Self-assembled alkanethiols that present oligo(ethyleneglycol) have been mixed with molecules possessing suitable linker groups, onto which bio-molecules can be attached for biosensor application [E. Ostuni, L. Yan, G. Whitesides, Colloids and Surfaces B: Biointerfaces 15 (1999) 3-30].

SUMMARY OF THE INVENTION

It is an object of the present invention to provide a method and biosensor for analysis with highly specific binding of analytes.

Biomolecule-repellent molecules with suitable terminal anchor groups on a monomer/polymer backbone, or a hydrophilic monomer/polymer "brush" bearing terminal anchor groups can be chemically grafted onto solids like Au, Ag, Cu, Al, Pd and GaAs to form a monolayer, together with biomolecules, especially immunological binder molecules (receptors), such as antibody fragments attached on the same surface. These biomolecule-repellent molecules are directly grafted on the same surface as the biomolecules, especially immunological binder molecules (receptors), such as antibody fragments, so that they form a mixed monolayer. The biomolecule-repellent molecules prevent the nonspecific binding of the analyte in the spaces left between the biomolecules. The immunoreactions can be detected with techniques like surface plasmon resonance, quartz crystal microbalance and impedance. The immobilization procedure will result in a significant reduction of the nonspecific binding of biological macromolecules of the analyte, because the surface between the Fab'-fragments will be highly hydrophilic and non-ionic, and, moreover, a proper orientation of the antibody fragment will result in a high binding of antigen.

Biomolecules, such as immunological binder molecules (receptors), can be immobilized in an oriented manner to provide a convenient method for analyzing quantitatively the analyte molecules attached to the biomolecules. One method of immobilization of antibody fragments is shown in O'Brien, J.; Jones, V.; Porter, M.; *Anal. Chem.* 72 (2000) 703, incorporated herein by reference.

In the analysis, a measuring method with which the substrate having a solid surface is compatible and which together with the substrate used is capable of giving a low detection limit is used. The solid surface, to which the biomolecule is directly bound together with the group having affinity towards the solid surface, is of the type that can induce a change in a signal, which is emitted to the substrate to interact with the combination of substrate, immobilized biomolecules and bound analyte, and subsequently detected, the signal change being indicative of an increase of a substance on the solid surface of the substrate (accumulation of the analyte molecules selectively bound to bio-molecules immobilized on the surface of the substrate).

The detection methods that are particularly suitable for achieving good sensitivity and when improve the performance of the method are surface plasmon resonance, thickness shear modes, surface acoustic waves and electro-chemical measurements.

BRIEF DESCRIPTION OF THE DRAWINGS

The objects and features of this invention will be better understood from the following description taken in conjunction with the drawings, wherein.

DETAILED DESCRIPTION OF PREFERRED EMBODIMENTS

A biomolecule is immobilized together with a functional group directly on a solid surface of a substrate to form a layer of oriented receptors for an analysis. The biomolecule can be a protein, a peptide, an enzyme, an antibody, a fragment of antibody (such as Fab'), an antigen, or a part of an antigen. For performing the analysis, these molecules should have a binding site specific for the analyte to be detected, and they will be designated also binder molecules or receptors hereinafter.

Biomolecules are attached directly to a solid surface of the substrate through a functional group, together with biomolecule-repellent monomer/polymer molecules attached to the same surface, so that the biomolecules become self-assembled on the surface with the active analyte-selective binding sites (such as antigen binding sites, epitopes or the like) being exposed, and the biomolecule-repellent molecules, also being self-assembled, cover the solid surface left between the biomolecules to prevent non-specific binding of the analyte molecules between the active binding sites of the biomolecules. Both the biomolecules and the biomolecule-repellent monomer/polymer possess functional groups having affinity for the solid surface of the substrate and acting as terminal anchor groups. For example organic molecules terminated by a sulfhydryl group can chemisorb on metals such as Au, Ag, Cu, Al and Pd surfaces through covalent bonds between the metal and the sulfur atoms and form a monolayer coating. Systems that exhibit self-assembly in the above-described manner include thiols, disulfides and sulfides that chemisorb spontaneously on metal surfaces through the sulfur containing functional groups.

If the method of analysis is a SPR measurement, the substrate used is a film of SPR-compatible material, such as gold, silver, copper, aluminum and palladium. However, the invention is not limited to any specific analytical method.

The biomolecule can be provided with the functional group by converting a structural part of it to the functional group, such as by reduction of a precursor group to a thiol. Alternatively, a linker molecule containing the functional group or a precursor thereof can be attached to the biomolecule to provide it with the functionality suitable for the self-assembly, and the biomolecule is subsequently made to chemisorb from a solution to the surface. The bio-molecules having the functional group are thereby adsorbed directly to the solid surface of the substrate in a single step to form the biosensor where the biomolecules form a monolayer in an oriented manner. The biomolecule-repellent monomer/polymer molecules are attached to the surface by chemisorption, also forming a monolayer in an oriented manner. The biomolecule-repellent molecules can be attached to the same surface either in the same step or subsequently to the immobilization of the biomolecules.

The biomolecule-repellent molecules can be attached to the surface by a simple chemisorption. The biomolecule-repellent molecules are preferably attached to the surface covalently through a suitable functional group (terminal anchor group), such as a sulfide, disulphide or thiol group at one end of the polymer chain. The biomolecule-repellent polymer used typically contains OH-groups at the opposite end. The combined forces of attraction, such as van der Waals' force, electrostatic force, entropic force and hydrogen-bonding force of the surface with the biomolecules to be repelled should be smaller than the entropic and hydrodynamic repulsion due to thermal motions of the flexible molecular chains on the solid surface and the biomolecules in the solution. Such surfaces can be prepared by immobilizing neutral, hydrophilic polymers, including polyacrylamide, poly-N,N-dimethylacrylamide, polyvinylalcohol, ethylene-vinylalcohol copolymer, poly-(hydroxyethylmethacrylate), poly(ethyleneoxide) and poly-(ethyleneglycol). Moreover, other polymers, such as polyethylene-telephthalate, polytetrafluoroethylene, polyurethane, etc., have been explored for their biocompatibility.

Figure 1:
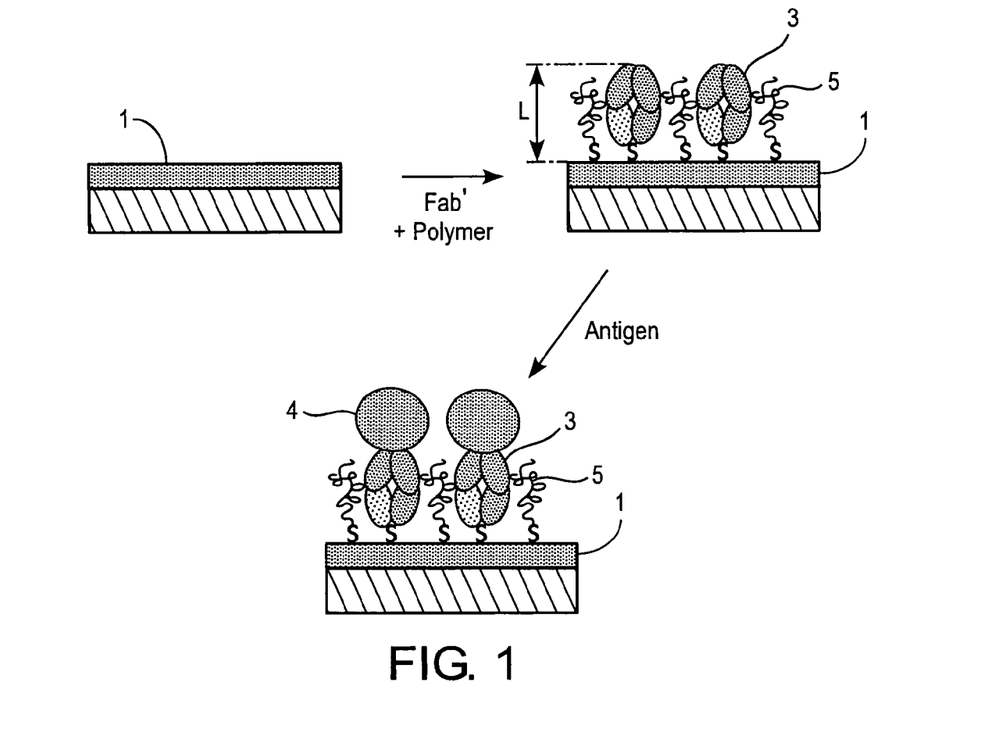
FIG. 1 is a schematic representation of a sensor surface where antibody Fab'-fragments together with biomolecule-repellent molecules are attached to a surface, and the interaction of the sensor with antigen.

According to one embodiment of the invention shown in FIG. 1, Fab'-fragments serving as receptors 3 are attached through the free thiol groups opposite the binding domain of the antibody, and/or antibodies/receptors with free thiol groups exposed are attached directly on a metal, semiconductor or (conducting) polymer surface or onto a mixture of these, i.e. a surface of a substrate 1, in sensor applications. Polymer molecules 5 creating a hydrophilic biomolecule-repellent surface are attached in an oriented manner to the same metal, semiconductor or (conducting) polymer surface where the receptors are bound, in the vacant spaces between the biomolecules, thus shielding the substrate surface from non-specific binding of the analyte molecules.

The term "biomolecule-repellent" means in this context repellent to the biomolecules in the analyzed solution to prevent the non-specific binding in between the receptor biomolecules.

The polymer molecules 5 are oriented so that their polymer chains project from the surface, their functional groups (such as thiol, sulfide or disulfide), serving as the attachment sites, being at the ends of the polymer chains. The thickness of the biomolecule-repellent molecule layer on the surface is preferably somewhat lower than the thickness L of the biomolecules (height of the biomolecules) on the surface of the substrate 1.

The solid substrate 1, to the outer surface of which the biomolecules serving as receptors 3 and the biomolecule-repellent polymer molecules 5' are attached, is a film of a suitable thickness and suitable material, which can be used for detection of an increased mass on its surface by one of the methods described hereinafter. An immunological reaction will take place between an analyte 4 (antigen) in solution brought in contact with the substrate 1 and the receptors 3 (Fab'-fragments) on the substrate 1. Detection of the analyte includes especially methods based on surface plasmon resonance, thickness shear mode resonator technique, one example of which is quartz crystal microbalance (0CM), surface acoustic waves (SAW devices) and electro-chemical measurements. The invention, using biomolecule-repellent mono-mer/polymer molecules to block non-specific binding sites between the specific binding sites of the biomolecules, is not, however, restricted to any specific analytical detection method.

Antibody fragments have been presented above as one example of biomolecules attachable to the surface. It is also within the scope of the present invention that the whole antibody is immobilized on the substrate surface for example through a free thiol group provided in its Fc region.

Figure 2:
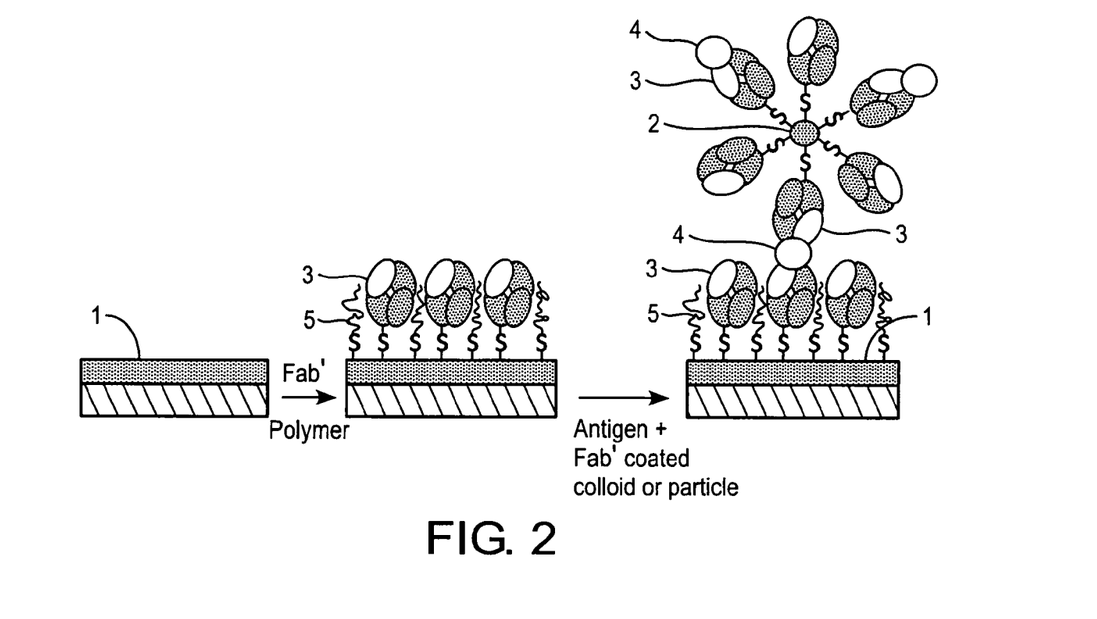
FIG. 2 is the representation of FIG. 1 showing the use of colloids/nanoparticles to amplify the detection.

According to another embodiment of the invention, the receptors 3/Fab'-fragments are used in a similar manner to coat separate particles 2, such as colloids and nanoparticles composed of the same materials as mentioned above, by attaching them through free thiol groups to the particles 2. These particles are used to amplify the detection signal when relatively small molecules and low concentrations of analyte have to be detected (FIG. 2). An immunological reaction will take place between analyte 4/antigen in the solution and receptors 3/Fab'-fragments on the substrate surface, and the analyte 4/antigen will, on the other hand, interact with the particles 2, to which the binder biomolecules are attached, such as the receptor/Fab'-fragment coated colloids/nanoparticles. Biomolecule-repellent polymer molecules 5 are used between the receptors 3 on the substrate surface in a similar manner as described above. A network of colloids/nanoparticles amplifying the signal will thus be formed. FIG. 2 shows how coated particles 2 become bound to the receptors 3 on the substrate surface through the analyte 4 (antigen). One example of such particles 2, to which the receptors 3 can be bound through free thiol groups, is gold particles.

Figure 3:
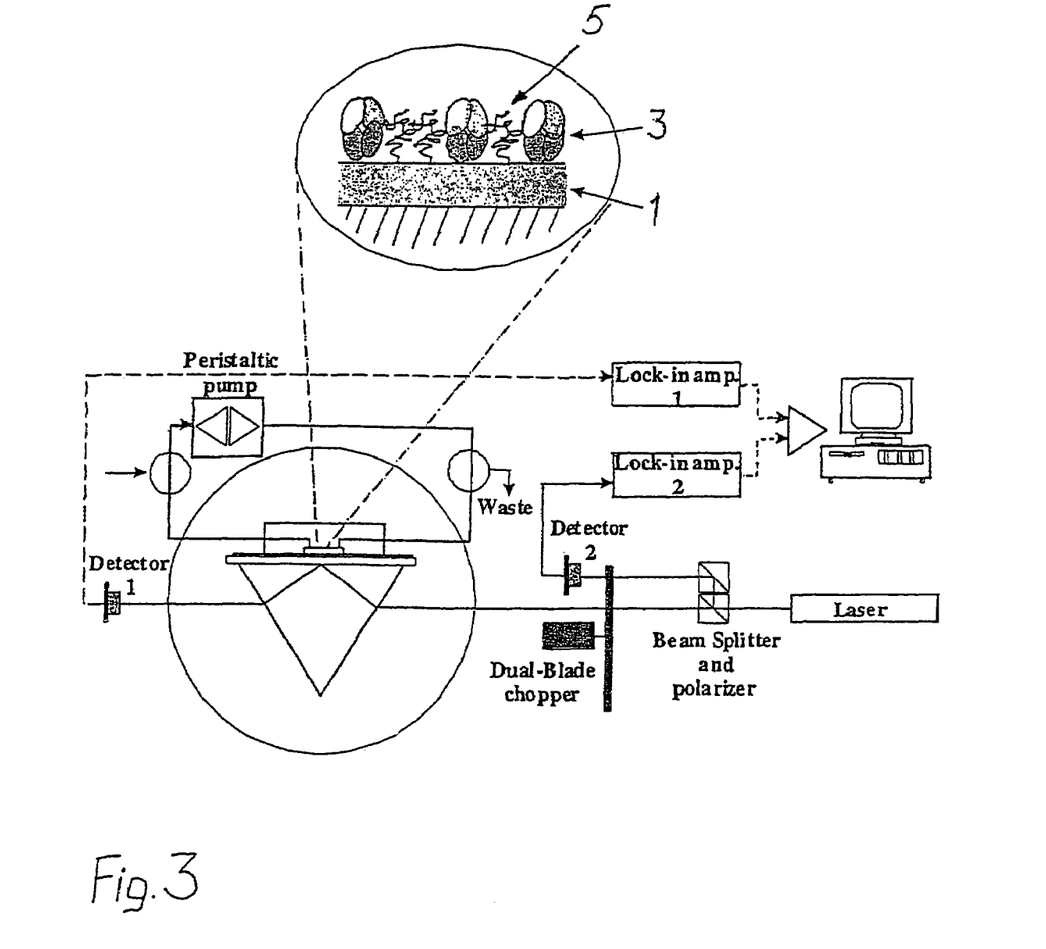
FIG. 3 shows a measurement set-up according to one embodiment of the invention.

FIG. 3 shows the principle of SPR measurement used in Example 1, and it also serves as an example of a biosensor according to one embodiment of the invention. As to the principles underlying the SPR measurement and properties of SPR compatible materials, reference is made for example to European Patent no. 537252 and to corresponding U.S. Pat. No. 5,322,798, incorporated herein by reference. The SPR configuration used has been described more closely by Sadowski et al. in *Opt. Eng.* 34 (1995) 2581-2586, incorporated herein by reference. Linearly p-polarized light of a wavelength of 632.8 nm from a He—Ne laser is directed through a prism onto a slide coated with a thin gold film positioned according to the well-known Kretschmann configuration. The intensity of the light is measured as a function of time at the particular angle where light is partly in resonance. Very small changes in light level can be measured by using two lock-in amplifiers at two different chopping frequencies to monitor light from the prism (sample beam) and from the laser (reference beam). Although in this case the dynamic range of SPR detection is limited, the method is particularly suited for measurements in liquid, where the resonance peak is rather broad. The Au substrate with the directly attached Fab'-fragments and biomolecule-repellent polymer was attached to the prism via an index matching oil. A flow cell was placed over the measurement area of the film and was filled with buffer. Protein solutions were pumped into the cell and changes in the intensity of the light were detected for about 10-15 mm at a suitable angle of incidence.

Figure 4:
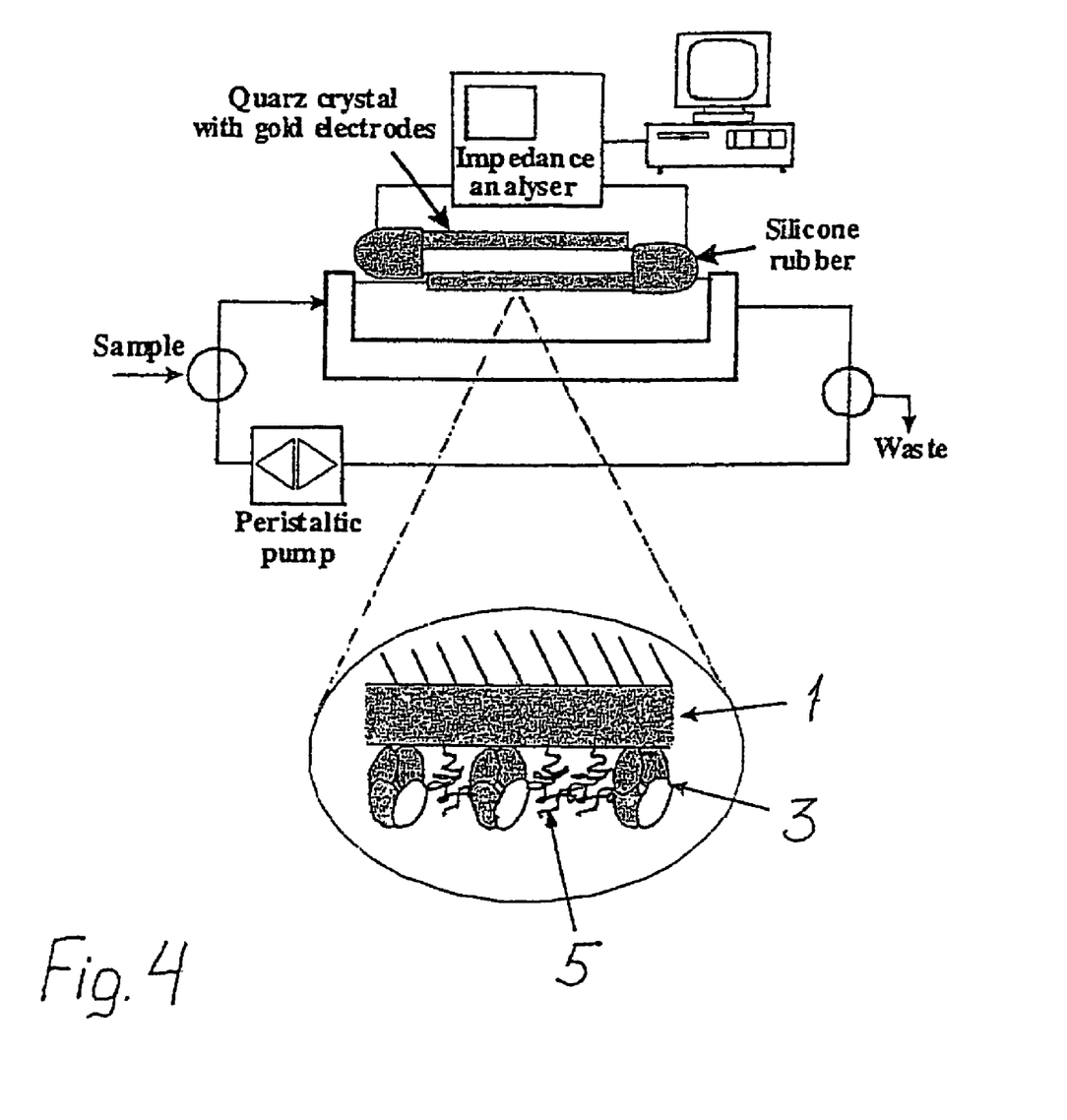
FIG. 4 shows a measurement set-up according to another embodiment of the invention.

FIG. 4 shows the principle of QCM measurement, which uses a thickness shear mode resonator principle, which can also be applied in the sensor according to the invention. As to the principles of the measurement, reference is made to the description in Vikholm, I.; Albers, W. M.; *Langmuir* 14 (1998) 3865, and incorporated herein by reference. The general principle underlying the detection method is the observation of decrease in the resonant frequency, which is proportional to the change in mass of the resonator due to the binding of the analyte to the biomolecules on the surface of one of the electrodes. The quartz crystal microbalance has electrodes consisting of electro-conducting layers 1 on both sides of the resonator crystal C. On the surface of one of the electrodes (electro-conducting layers 1) the biomolecules 3 and the biomolecule-repellent polymer molecules 5 have been immobilized for example in the manner shown in FIG. 1, and this electrode face is placed in contact with the solution containing the analyte to be detected. The edges of the resonator are covered with silicone rubber to protect the wires and electrical contacts. The detection is performed by electrical resonance measurement, and a spectrum/network analyzer connected to a computer can be used to determine the resonant frequency.

Other feasible methods of detection include the use of surface acoustic wave devices or electrochemical quartz crystal microbalances.

As a conclusion, according to this invention biomolecule-repellent molecules and antibody Fab'-fragments can be covalently grafted on metal surfaces to give a surface reactive towards the specific antigen. The use of hydrophilic polymers together with the Fab'-fragments leads to a surface with low non-specific binding, thus improving the sensitivity and selectivity of the immunoassay. This technique could, moreover, be easily applied in multi-array screening by photopatterning of the surface.

In the following, some tests exemplifying the invention are described, which do not restrict the scope of the invention.

EXAMPLE 1

The model antibody was polyclonal goat anti-human F(ab')$_2$ (Jackson ImmunoResearch, chromatically purified) with minimized cross-reaction to bovine, horse, and mouse serum proteins. The antigen was chromatically purified human IgG (Jackson ImmunoResearch). F(ab')$_2$ was split into Fab'-fragments with dithiothreitol (DTT, Merck) prior to use as follows: F(ab')$_2$ with a concentration of 1.2-1.3 mg/ml (100 μl) was mixed with 50 μl of HEPES/EDTA buffer (150 mM NaCl, 10 mM HEPES, 5 mM EDTA, pH=6.0) and 10 μl of a 0.1 M DTT solution in HEPES/EDTA buffer in a microdialysis tube. The dialysis tube was immersed in 250 ml of argon-purged HEPES/EDTA buffer and dialyzed for about 18 h at room temperature under argon. The Fab'-fragment was maintained under argon and used immediately for attachment.

Fab'-fragments have well-accessible reactive thiol groups opposite the antibody binding domains.

A Surface Plasmon Resonance device, SPRDEVI was used for the measurements (VTT, Tampere). The glass slides used were coated with thin films of titanium (4 nm, to increase the adhesion of gold) and gold (37 nm) by vacuum evaporation. The slides were cleaned immediately before use in a hot solution of 1:1:5 $H_2O_2:NH_4OH:H_2O$ and rinsed with water. The slides were attached to the SPR prism via an index matching oil, the flow cell was assembled on the prism and 10 mM HEPES, 150 mM NaCl, pH 7.2 was allowed to flow through the cell. High purity water (18.2 MΩcm) from a Milli-Q system (Millipore Co., Bedford, USA) was used for the preparation of buffer solutions. SPR intensity curves were recorded and in situ measurements were taken at a fixed angle corresponding to the steepest point of the SPR curve. The bio-molecule-repellent polymer monolayer was based on an N-[tris(hydroxy-methyl)methyl]acrylamide monomer and grafted to the gold surface through di-sulfide anchors at a concentration of 0.12 mg/ml. The Fab'-fragments were immobilized onto the surface and hereafter the biomolecule-repellent molecules were grafted onto the same surface.

Figure 5:
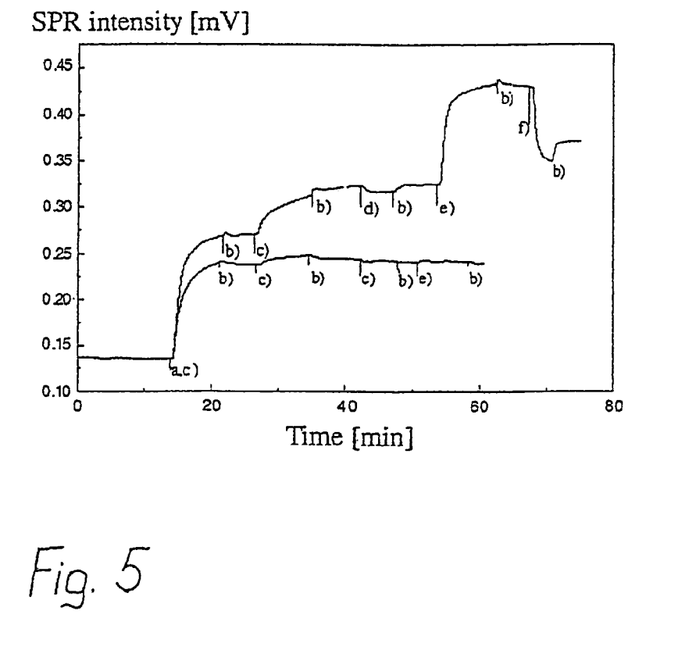
FIG. 5 shows the change in SPR on attachment of various macromolecules onto a thin gold film.

FIG. 5 is a typical SPR sensorgram showing the change in SPR intensity on attachment on various molecules onto the surface. The upper curve represents the forming and behavior of the combined monolayer of the receptors 3 (Fab'-fragments) and the biomolecule-repellent polymer molecules 5, and the lower curve represents the monolayer consisting only of the biomolecule-repellent polymer molecules 5. The moments of attachment of the Fab'-fragments and the biomolecule-repellent polymer molecules are denoted with letters a and c, respectively. The moment of adding bovine serum albumin (BSA) is denoted with letter d.

The sensorgram shows the initial fast increase of the SPR intensity on grafting of Fab'-fragments or the biomolecule-repellent polymer to gold leading to a plateau value, followed by a slow desorption of irreversibly bound Fab'-fragments or polymer at the rinsing phase (rinsing with buffer is denoted with b). The biomolecule-repellent polymer can, moreover, be grafted onto the surface, onto which Fab'-fragments already have been attached (point c in the upper curve). The polymer is supposed to be attached in between the bound Fab'-fragments, thus shielding the gold surface from non-specific binding of biomolecules. There is no adsorption of BSA to the pure polymer layer and only a minor increase in SPR intensity is observed with the antibody/polymer layer on adsorption of BSA (point d). Some BSA molecules might be adsorbed close to the antibodies. There is a large increase in the SPR intensity on injection of hIgG onto the Fab'/polymer layer (point e in the upper curve), but no change in the intensity can be observed, if antibody was not included on the pure polymer layer (point e in the lower curve). The antibody layer can, more-over, be regenerated with a HCl-glycine solution, which shows that an immunoreaction had taken place (point f in the upper curve).

Figure 6:
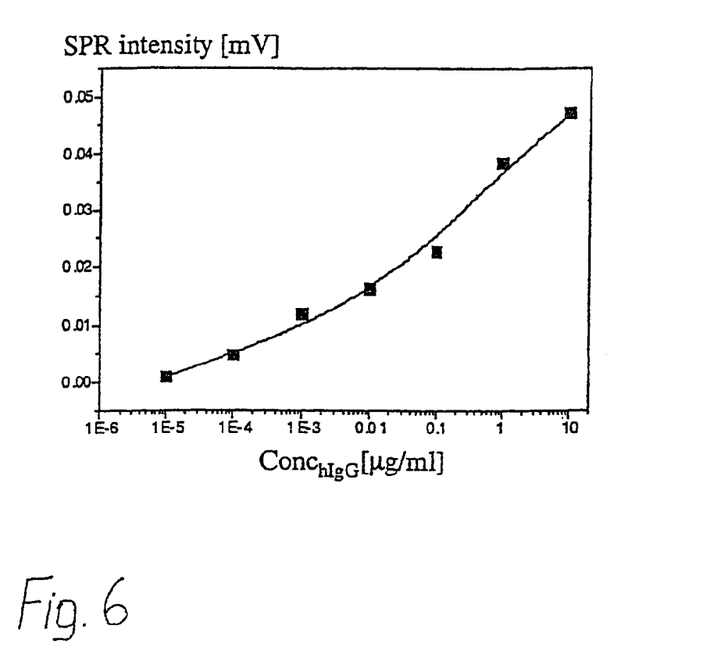
FIG. 6 shows a SPR binding isotherm obtained with a sensor according to the invention.
Figure 7:
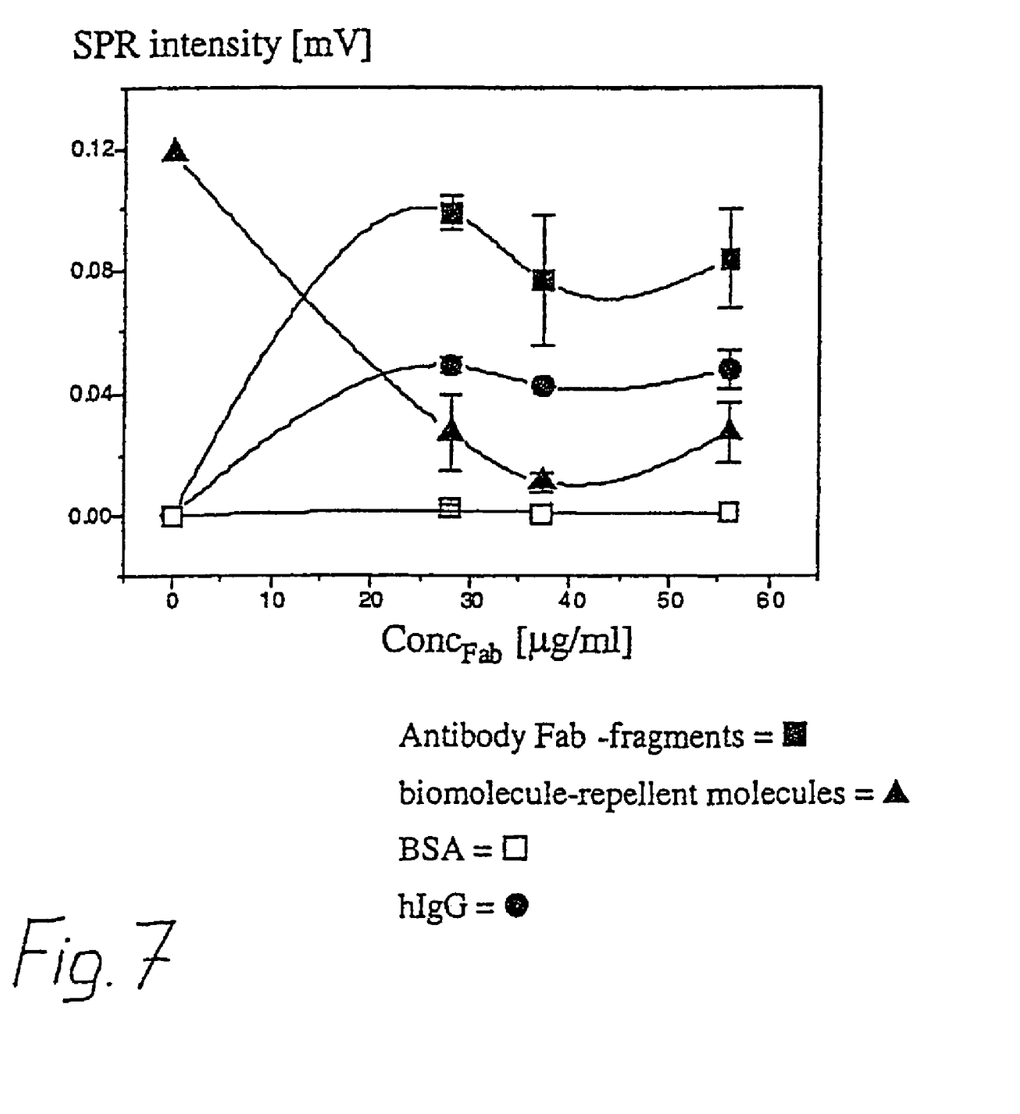
FIG. 7 shows the total shift in SPR intensity or binding of various macromolecules onto a thin gold film.

The SPR binding isotherm of hIgG on the combined monolayer of Fab'-fragments and biomolecule-repellent polymer has been measured in a concentration range of 1 pg/ml-10 µg/ml (FIG. 6). In FIG. 7 the shift in the SPR intensity caused by antibody Fab'-fragments, biomolecule-repellent molecules, BSA, and hIgG is shown as a function of Fab'-fragment concentration on sub-sequent binding of the antibody Fab'-fragments, biomolecule-repellent molecules, BSA, and hIgG on the thin gold film. The amount of biomolecule-repellent molecules grafted decreases with amount of antibody fragments bound. The non-specific binding of BSA is nearly independent on antibody concentration. Binding of hIgG reaches a plateau value at the Fab'-fragment concentrations studied.

The invention claimed is:

1. A method for analysis, comprising:
   binding analytes (4) in a sample to biomolecules (3) attached to a solid surface of a substrate (1); and
   detecting the analytes bound to the biomolecules; wherein:
   the biomolecules (3) are attached directly in an oriented manner to the substrate together with biomolecule-repellent molecules (5); and
   the biomolecule-repellent molecules are covalently attached to the substrate through functional groups and are self-assembled on the surface to cover the surface between the biomolecules (3) to prevent non-specific binding of analytes (4) and other biomolecules.

2. The method of claim 1, wherein the functional groups are selected from the group consisting of: sulfide, disulfide and thiol groups.

3. The method of claim 1, wherein the substrate is a sensor substrate capable of inducing a change in a signal, indicative of an increase of an analyte (4) bound to the biomolecules (3) on its surface, the signal is applied to the substrate (1), the changed signal is detected, and the quantity of the analyte (4) bound to the biomolecules (3) on the surface of the substrate (1) is measured by means of the detected signal.

4. The method of claim 1, wherein in addition to biomolecules (3) and biomolecule-repellent molecules (5) attached directly to the surface of the substrate (1), separate particles (2) containing immobilized biomolecules are attached to the substrate through analytes (4) bound to said biomolecules (3) on the substrate (1).

5. The method of claim 1 or claim 4, wherein the biomolecule (3) is a protein, a peptide, an enzyme, an antibody, a fragment of an antibody, an antigen or a part of an antigen, and the biomolecules are attached through thiol, disulfide or sulfide groups to the surface of substrate (1) and/or particles (2).

6. The method of claim 1, wherein the biomolecule-repellent molecules (5) are polymers.

7. The method of claim 1, wherein the substrate (1) is a surface plasmon resonance (SPR) compatible material, and the analysis is performed by SPR measurement.

8. The method of claim 1, wherein the analysis is performed by a thickness shear mode resonator.

9. The method of claim 8, wherein the thickness shear mode resonator is a quartz crystal microbalance (QCM).

10. The method of claim 1, wherein the substrate (1) is a metal, a semiconductor or an electrically conductive polymer.

11. The method of claim 1, wherein the biomolecules (3) are immunological binder molecules, and the analysis is an immunological analysis.

12. The method of claim 11, wherein the immunological binder molecules are antibodies or immunologically active fragments thereof.

13. The method of claim 6, wherein the polymers are hydrophilic polymers.

14. The method of claim 6, wherein the polymers are selected from the group consisting of: polyacrylamide, poly-N,N-dimethylacrylamide, polyvinylalcohol, ethylenevinylalcohol copolymer, poly-(hydroxyethylmethacrylate), poly-(ethyleneoxide), poly-(ethyleneglycol), polyethylenetelephthalate, polytetrafluoroethylene, and polyurethane.

15. The method of claim 14, wherein the polymers are selected from the group consisting of: polyacrylamide, poly-N,N-dimethylacrylamide, polyvinylalcohol, ethylenevinylalcohol copolymer, poly-(hydroxyethylmethacrylate), poly-(ethyleneoxide), and poly-(ethyleneglycol).

16. The method of claim 6, wherein the polymers are poly-(N-[tris(hydroxymethyl)methyl]acrylamide).

17. A biosensor for analysis, comprising a substrate and biomolecules (3) attached to a substrate (1), wherein:
the biomolecules (3) are attached directly in an oriented manner to the substrate together with biomolecule-repellent molecules (5);
the biomolecule-repellent molecules are covalently attached to the substrate through functional groups and are self-assembled on the surface to cover the surface between the biomolecules (3) to prevent non-specific binding of analytes (4) and other biomolecules; and
the biosensor is a thickness shear mode resonator sensor.

18. The biosensor of claim 17, wherein the thickness shear mode resonator sensor is a quartz crystal microbalance (QCM) sensor.

* * * * *